(12) United States Patent
Montaser et al.

(10) Patent No.: US 7,804,064 B2
(45) Date of Patent: Sep. 28, 2010

(54) IN-SITU DROPLET MONITORING FOR SELF-TUNING SPECTROMETERS

(75) Inventors: Akbar Montaser, Potomac, MD (US); Kaveh Jorabchi, Arlington, VA (US); Kaveh Kahen, Kleinburg (CA)

(73) Assignee: The George Washington University, Washington, DC (US)

( * ) Notice: Subject to any disclaimer, the term of this patent is extended or adjusted under 35 U.S.C. 154(b) by 1163 days.

(21) Appl. No.: 11/240,642

(22) Filed: Oct. 3, 2005

(65) Prior Publication Data

US 2006/0087651 A1    Apr. 27, 2006

Related U.S. Application Data

(60) Provisional application No. 60/615,542, filed on Oct. 1, 2004.

(51) Int. Cl.
*H01J 49/00* (2006.01)
(52) U.S. Cl. .................. 250/288; 250/281; 250/282
(58) Field of Classification Search ......... 250/281–300, 250/574
See application file for complete search history.

(56) References Cited

U.S. PATENT DOCUMENTS

| | | | | |
|---|---|---|---|---|
| 5,101,113 | A * | 3/1992 | Hirleman et al. ............ | 250/574 |
| 6,355,570 | B1 * | 3/2002 | Nakata et al. ............... | 438/706 |
| 6,496,258 | B1 * | 12/2002 | Leipertz et al. ............. | 356/336 |
| 6,576,559 | B2 * | 6/2003 | Nakata et al. ............... | 438/706 |
| 6,609,412 | B2 * | 8/2003 | Dimarzo et al. ............ | 73/25.01 |
| 6,712,928 | B2 * | 3/2004 | Nakano et al. ......... | 156/345.24 |
| 7,078,712 | B2 * | 7/2006 | Perel et al. ............. | 250/492.21 |
| 7,126,687 | B2 * | 10/2006 | Hill et al. .................... | 356/336 |
| 7,167,240 | B2 * | 1/2007 | Stagg .......................... | 356/337 |
| 7,260,483 | B2 * | 8/2007 | Gard et al. ..................... | 702/22 |
| 2001/0040214 | A1 * | 11/2001 | Friedman et al. ............ | 250/287 |
| 2002/0016068 | A1 * | 2/2002 | Nakano et al. .............. | 438/689 |
| 2002/0094685 | A1 * | 7/2002 | Nakata et al. ............... | 438/689 |
| 2003/0223063 | A1 * | 12/2003 | Hill et al. ..................... | 356/340 |
| 2004/0046957 | A1 * | 3/2004 | Stagg .......................... | 356/335 |
| 2005/0205807 | A1 * | 9/2005 | Perel et al. ............. | 250/492.21 |

* cited by examiner

*Primary Examiner*—Bernard E Souw
*Assistant Examiner*—Andrew Smyth
(74) *Attorney, Agent, or Firm*—Roylance, Abrams, Berdo & Goodman, L.L.P.

(57) ABSTRACT

A laser scattering based imaging technique is utilized in order to visualize the aerosol droplets in an inductively coupled plasma (ICP) torch from an aerosol source to the site of analytical measurements. The resulting snapshots provide key information about the spatial distribution of the aerosol introduced by direct and indirect injection devices: 1) a direct injection high efficiency nebulizer (DIHEN); 2) a large-bore DIHEN (LB-DIHEN); and 3) a PFA microflow nebulizer with a PFA Scott-type spray chamber. Moreover, particle image velocimetry (PIV) is used to study the in-situ behavior of the aerosol before interaction with, for example, plasma, while the individual surviving droplets are explored by particle tracking velocimetry (PTV). Further, the velocity distribution of the surviving droplets demonstrates the importance of the initial droplet velocities in complete desolvation of the aerosol for optimum analytical performance in ICP spectrometries. These new observations are important in the design of the next-generation direct injection devices for lower sample consumption, higher sensitivity, lower noise levels, suppressed matrix effects, and for developing smart spectrometers. For example, a controller can be provided to control the output of the aerosol source by controlling the configuration of the source or the gas flow rate via feedback information concerning the aerosol.

43 Claims, 7 Drawing Sheets

200

IN-SITU DROPLET MONITORING FOR SELF-TUNING SPECTROMETERS

CROSS REFERENCE TO A RELATED PATENT AND CLAIM TO PRIORITY

Related subject matter is disclosed in U.S. Pat. No. 6,166,379, entitled "Direct Injection High Efficiency Nebulizer For Analytical Spectrometry", issued on Dec. 26, 2000 to Akbar Montaser et al. This application claims benefit under 35 U.S.C. §119(e) of provisional patent application Ser. No. 60/615,542 filed on Oct. 1, 2004. The entire disclosures of said patent and provisional application are hereby incorporated by reference.

This application was made with United States Government Support under Grant No. DE-FG02-93ER14320 awarded by the U.S. Department of Energy and under Grant Nos. CHE-9505726 and CHE-9512441 awarded by the National Science Foundation. The U.S. Government has certain rights in the invention.

BACKGROUND OF THE INVENTION

1. Field of the Invention

This application relates generally to nebulizers for use in analytical spectrometry such as inductively coupled mass spectrometry, as well as to fuel injector systems, inhalers, and the like. More specifically, the present invention is directed to methods for monitoring and controlling droplets and their characteristics in order to, for example, optimize spectrometer operating parameters to improve stability of an analytical signal and/or enhance the signal. (Throughout the specification the terms "droplets", "aerosol" and "particles" may be used interchangeably.)

2. Description of the Related Art

Flame and plasma spectrometers are commonly used to analyze samples for their transferred into a liquid phase by procedures such as dissolution in proper solvents. The test solution is then converted into a mist by means of a variety of nebulizers, with the pneumatic ones being the most common. The mist is introduced into the hot source (i.e. flame or plasma) and undergoes sequential steps of desolvation, vaporization, atomization, excitation and ionization. The resulting atoms and ions may then be monitored by atomic absorption, atomic emission or mass spectrometric methods.

Among the steps cited above, desolvation is the most critical step and exerts the largest effect on the stability and the magnitude of the detected signal, the precision and the accuracy of the analytical measurement. Incomplete desolvation of the droplets or imperfect evaporation of the dried particles in the source results in local cooling in the analytical zone of the plasma or flame, leading to higher noise levels, reduced signal, and increased matrix effects.

Desolvation of the droplets is controlled by the quality of the aerosol droplets (i.e. size, velocity and spatial distribution in the source) and the source characteristics (e.g. temperature) governed by the plasma or flame operating conditions (e.g. operating power, chemical compositions of gases forming the plasma or flame, gas flow rates, height of analytical measurements).

In current spectrometers, constant operating parameters are maintained throughput the analysis from optimization of the analytical signal for a well-characterized standard solution as close as possible to the test solution in terms of composition. Therefore, changes in the test solution that require a new optimum operating set (e.g. change in the solvent composition) will result in alteration of the analytical signal. Due to the unknown nature of most sample solutions (e.g. environmental samples, biological materials), correction for the changes is exceedingly complex, requiring extensive sample preparation procedures, which is usually time and labor expensive, and may cause contamination of the samples.

Inductively coupled plasma (ICP) spectrometry is the current method of choice for elemental and isotopic analysis.[1-3] Despite years of research and remarkable improvements in instrumentation, sample introduction is still the main problem of this powerful analytical tool. In pneumatic nebulization, the most popular method of solution introduction in ICP spectrometry, an aerosol is produced as a result of interactions between the liquid sample and a gas flow at the nebulizer nozzle.[4-8] The nebulizer is typically coupled to a spray chamber to remove the coarse droplets prior to introduction of aerosol into the plasma. However, spray chambers suffer from low transport efficiencies, loss of volatile analyte, and increased memory requirements and transient acid effects.[4,8-10] To alleviate these drawbacks, a test solution is directly injected into the ICP through devices such as the direct injection nebulizer (DIN) and the direct injection high efficiency nebulizer (DIHEN).[11,12] Furthermore, direct injection devices offer reduced dead volume necessary for chromatography and capillary electrophoresis, minimizing the post-column broadening and improving the separation efficiency.[13-16]

In both direct and indirect (conventional) sample introduction methods, the quality of the aerosol determines its fate inside the plasma, profoundly affecting the analytical performance. Ideally, the droplets must be small and slow moving, uniform in size and velocity, and confined to the central channel of the ICP. These properties lead to optimum conditions for efficient desolvation, vaporization, atomization, excitation, and ionization of the analyte in the plasma, resulting in the best analytical performance. Conventional pneumatic nebulizers, however, generate a polydisperse aerosol,[17-24] leading to inefficient desolvation in the plasma. The presence of the incompletely desolvated droplets in the analytical zone of the plasma disturbs the steady-state signal generation in both ICP atomic emission spectroscopy (ICPAES) and ICP mass spectrometry (ICPMS), resulting in higher noise levels, reduced signal, and increased matrix effects.[25-30]

The fate of the droplets in the plasma may be studied using high-speed photography or time-resolved spectroscopic techniques.[25-35] The latter can provide the axial velocity of the atomic or ionic clouds around the droplets and analyte particles in the ICP. However, the cited clouds are typically much larger e.g., a few mm than the droplets e.g., a few μm and generally have the gas velocity of 20-25 m/s and cannot, thus, offer direct information on the size and velocity of the droplets inside the plasma. Recently, planar dropsizing and particle image velocimetry (PIV) have been utilized to characterize the size and velocity of the droplets and particles in glow discharge plasmas and flames.[36,37] Also, a laser based imaging method has been developed to measure the size of the droplets in a thermal reactor.[38] However, the source gas temperature in these studies was much lower than that of typical argon ICP, and the droplets were at least one order of magnitude larger than those encountered in ICP spectrometries. Small droplets (<30 μm) in high-temperature ICP (3000-7000 K) provide a challenging environment for the experimental study and optimization of the physical phenomena underlying this extremely sensitive and selective analytical technique.

Theoretical simulations are the only source of information about the characteristics of the droplets inside ICPs[39-43].

Importantly, no direct experimental method is available to verify the theoretical predictions to further develop the models.

Despite 100% transport efficiency, the current direct injection devices offer less than optimum spatial focusing of the aerosol into the central channel of the ICP, resulting in signal loss, elevated noise levels, matrix effects, and post-column broadening in hyphenated techniques. On the other hand, indirect sample introduction methods suffer from lower transport efficiencies, large dead volume, and spray-chamber induced matrix and memory effects, however, the droplets strictly travel in the axial channel due to the injector tube of the ICP torch. In both cases, the droplet velocities do not match the gas velocity in the axial channel. Indirectly introduced droplets lag behind the gas flow while directly injected ones exceed the gas velocity.

Directly introduced aerosols are highly scattered across the plasma torch as a result of their rotational behavior, indicating less than optimum sample consumption efficiency for the current direct injection devices.

A need exists for a system and method that provides novel insights on the behavior of the sample droplets inside an argon ICP through direct imaging of the droplets, from the tip of the nebulizer or injector to the normal analytical zone of the plasma.

In the system and method, Mie scattering from water droplets is used for imaging, providing remarkable insights into spatial distribution and evaporation of the droplets produced by three diverse sample introduction systems: 1) the DIHEN, 2) the large bore DIHEN (LB-DIHEN),[44] and 3) a micronebulizer-spray chamber arrangement. Also, PIV and particle tracking velocimetry (PTV) are applied to further probe the velocity of the droplets before and after interaction with the plasma, respectively.

SUMMARY OF THE INVENTION

A laser-based imaging technique has been developed to visualize and contrast the properties of droplets in a high temperature ICP using direct and indirect pneumatic sample introduction techniques. The technique is novel because it provides simultaneous information on the in-situ location, velocity distribution, and the number of the droplets in the high-temperature plasma, revealing their eventual contribution to analytical signal or noise in ICP spectrometries.

In pneumatic nebulization, higher gas flow rates are required to produce fine droplets, however, such high flows yield fast droplets that may survive the plasma. This trade-off is particularly important for direct injection devices where no filtering is performed on the aerosol before their introduction into the ICP. For the best analytical performance, small droplets must be focused into the axial channel of the ICP at low velocities (<15 m/s), and via a narrow cone, much narrower than the aerosol cone provided by the current direct injection nebulizers. A longer torch may also be used to accommodate a longer residence time for directly introduced droplets. However, the prediction of an optimum length requires a detailed knowledge on both size and velocity of the droplets throughout the plasma. The exemplary techniques described herein in the context of certain embodiments of the present invention, may be utilized for online monitoring of the droplet characteristics during the analysis. Such an arrangement provides an opportunity to use direct observations on the droplets as a feedback signal for further optimization, resulting in smart spectrometers.

A droplet (particle) monitoring self-tuning spectrometer according to an embodiment of the present invention uses the in-situ characteristics of the droplets to maintain the optimum characteristics of the aerosol introduced into the source by automatically adjusting the droplet generation process or source operating conditions. Such an arrangement facilitates: 1) a more stable analytical signal, improving the accuracy and precision of the analytical measurement, and 2) reduced manpower and time necessary for obtaining an acceptable analytical assessment.

BRIEF DESCRIPTION OF THE DRAWINGS

Certain exemplary aspects and features of the present invention will be more apparent by describing certain embodiments of the present invention with reference to the accompanying drawings, in which.

DETAILED DESCRIPTION OF EXEMPLARY EMBODIMENTS

The concepts and devices presented here can be used to monitor droplets and their characteristics as they undergo desolvation and evaporation in a plasma or a flame source. This information (e.g. droplet number density, droplet size and velocity) can then be used as a feedback signal to optimize the droplet generation and/or source and spectrometer operating parameters to obtain a stable analytical signal. Although in an embodiment of the present invention, the in-situ measurements described below are centered on an inductively coupled plasma source, it should be appreciated by those skilled in the art that the in-situ measurements are equally applicable to other sources.

To illustrate the potentials of the proposed technique in creating data suitable for tunable spectrometer, the droplet size and velocity information is presented for three diverse nebulization systems. The nebulization systems include: 1) a direct injection high efficiency nebulizer (Model DIHEN-170-AA, manufactured by Meinhard Glass Products, Analytical Reference Materials International Corp., Golden, Colo.) as described by A. Montaser, J. A. McLean, J. M. Kacsir, A Novel Direct Injection High Efficiency Nebulizer for Atomic Spectroscopy, U.S. Pat. No. 6,166,379 (2000) and J. A. McLean, H. Zhang, A. Montaser, A Direct High Efficiency Nebulizer for Inductively Coupled Plasma Mass Spectrometry, *Anal. Chem.* 70, 1012-1020 (1998); 2) a large bore-DIHEN (Model LB-DIHEN-30-AA, Large Bore Direct Injection High Efficiency Nebulizer for Inductively Coupled Plasma Spectrometry, *Anal. Chem.* 72, 1885-1893 (2000); and 3) a fixed-capillary microflow nebulizer (Model PFA-100, Elemental Scientific, Inc., Omaha, Nebr.) with a Scott-type spray chamber (Model PureChamber, Elemental Scientific, Inc.) both made from PFA, all of which are incorporated herein in their entirety.

Figure 1:
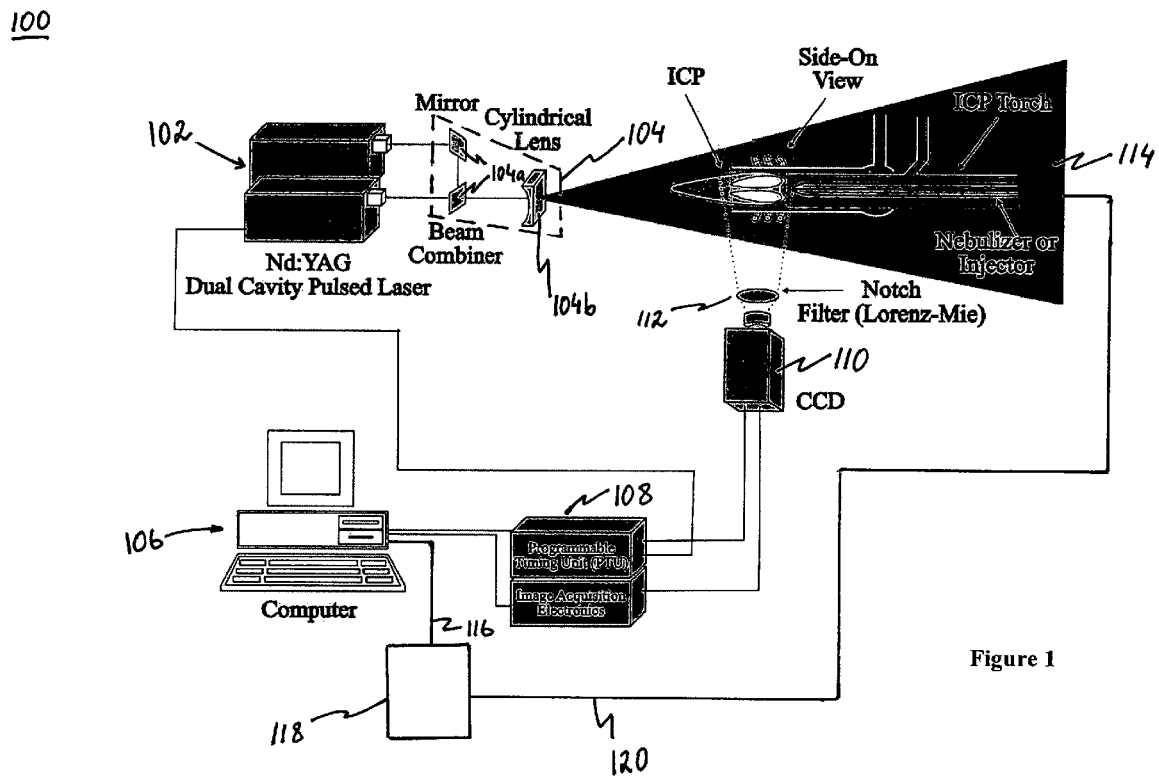
FIG. 1 is a schematic diagram illustrating an experimental setup for in-situ visualization and characterization of aerosol droplets in an inductively coupled plasma in accordance with an embodiment of the present invention.

The exemplary monitoring system 100 of FIG. 1 comprises a dual cavity frequency-doubled Nd: YAG pulsed laser 102 and a set of cylindrical lenses 104 comprising mirrors 104a and a cylindrical lens 104b in order to generate a laser sheet of about 1-mm thickness which slices the plasma at a desired position.

The system 100 further comprises a computer 106, a programmable timing unit and image acquisition unit 108, a charge coupled detector (CCD) 110, a notch filter 112, a nebulizer or injector 114, a feedback line 116, a controller 118, and a control line 120. The feedback line 116 connected between the computer 106 and the controller 118 represents momentum, which is defined as mass times velocity. That is, the amount of aerosol is monitored via the system 100. The feedback from the nebulizer 114 via feedback line 116, controller 118 and control line 120 may be used to control the critical dimensions of nebulizer 114 such as the gas flow rate and the nebulizer tip.

The scattered light from the droplets traveling in the plasma is recorded by a cross-correlation charge coupled detector (CCD) 110 preferably accompanied by a 60-mm focal length lens positioned at 90° angle with respect to the laser sheet. Background levels are reduced using the narrow band-pass notch filter 112 in the optical path.

In order to examine the velocity of the individual surviving droplets, the exposure time of the CCD 110 is adjusted to capture the scattering of two laser pulses, fired with a known time lag $\Delta t=50$ μs, on the same image. The distance between the droplet pairs in the resulting image provides their displacement during the 50-μs time interval, allowing measurements of the velocity in x and y directions ($V_x$, $V_y$) from $\Delta x/\Delta t$ and $\Delta y/\Delta t$ as shown in FIG. 2.

Figure 2:
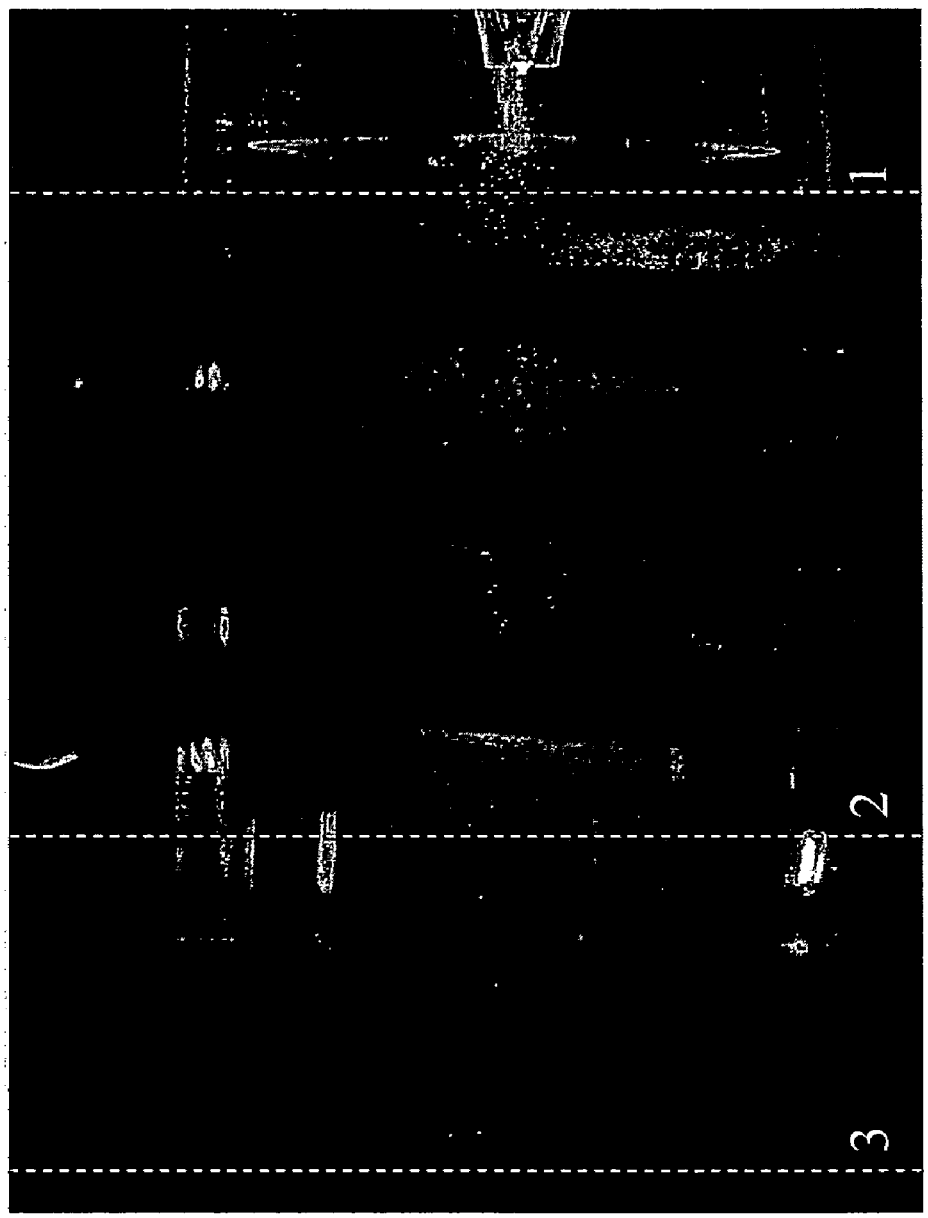
FIG. 2 is a side-on snapshot illustrating droplets introduced by direct injection high efficiency nebulizer (LB-DIHEN) inside an Ar ICP where position 1 represents 1-mm above the intermediate tube, position 2 represents a last turn of the load coil, and position 3 represents a typical location of a sampler in an ICPMS e.g., 10 mm above the load coil.

FIG. 2 shows a side-on snapshot of the ICP torch with three dashed lines, illustrating critical positions and terms. Line 1 marks 1-mm downstream the intermediate tube where the aerosol enters into the plasma. End-on imaging of the torch is performed with the laser sheet fired at position 1 to study the in-situ behavior of the droplets in the presence and absence of the plasma as they emerge from the nozzle. Line 2 corresponds to the top turn of the load coil. The droplets passing Line 2 are considered to be "surviving droplets" (see 3 droplets in FIG. 2), and are more likely to contribute to higher noise levels, loss of signal, physical and chemical interferences, and matrix effects. Finally, Line 3 depicts the typical location of the sampler located 10-mm above the load coil in ICPMS, where the ions are extracted into the vacuum interface. The shadow of the nebulizer in FIG. 2 is due to light reflection from the inner surface of the intermediate tube. To determine the width of the axial channel, an exposure time of 50 μs is used to capture some of the plasma background emission in the image shown in FIG. 2.

Figure 3:
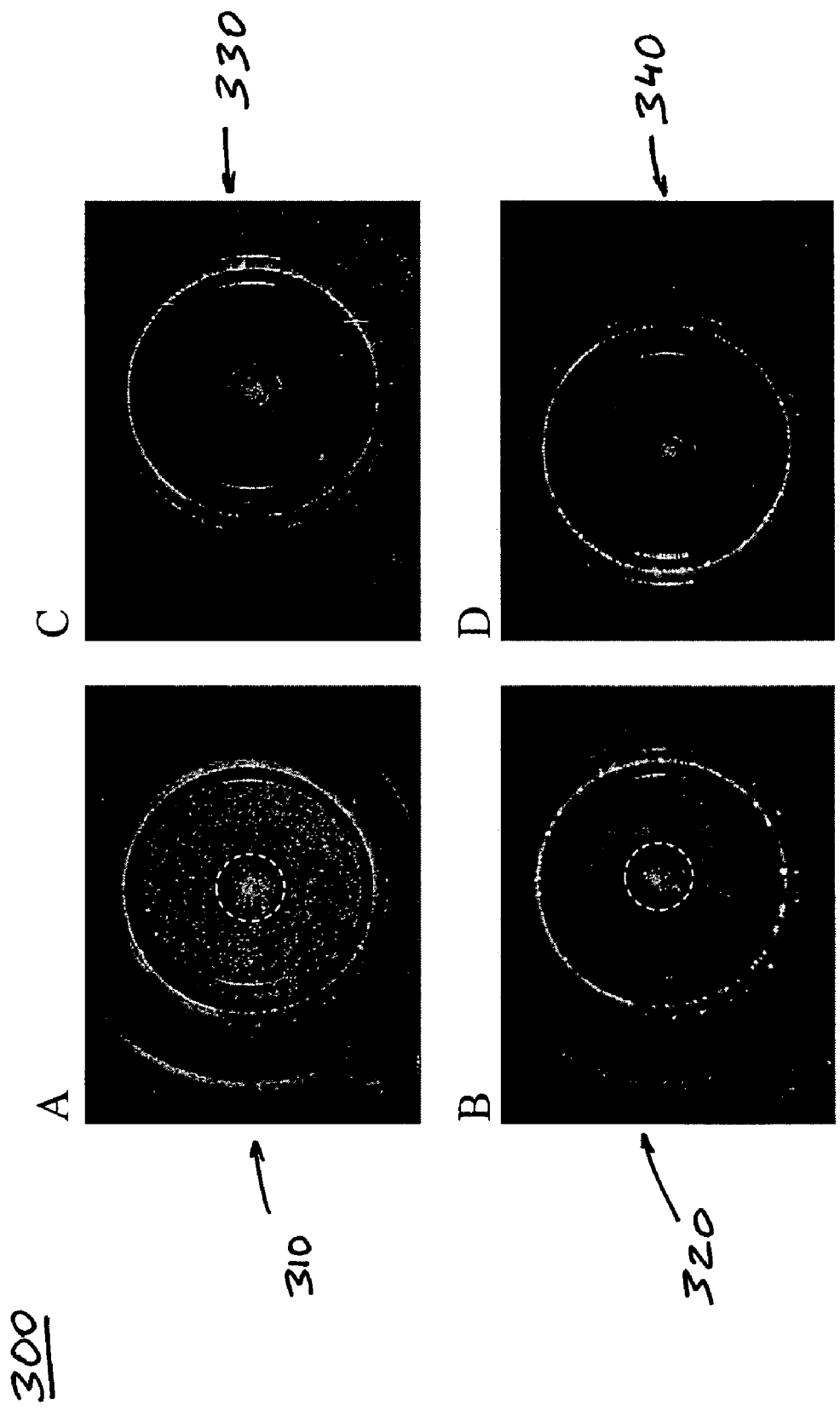
FIG. 3 is an end-on view illustrating the droplets inside the torch in the absence and presence of the plasma with the laser sheet fired at position 1; A) DIHEN, Plasma off, B) and presence of the plasma with the laser sheet fired at position 1; A) DIHEN, Plasma off, B) DIHEN, Plasma on, C) PFA-Spray chamber, Plasma off, and D) PFA-Spray chamber, Plasma on wherein the 5-mm i.d. dashed circle indicates the approximate location of the axial channel.

Characteristics of an aerosol inside an ICP torch and direct vs. indirect nebulization will now be discussed. Spatial distribution of the droplets immediately above the intermediate tube, just prior to their interaction with the ICP, substantially affects the analytical figures of merit. FIG. 3 shows the velocity distribution of surviving droplets generated by three diverse nebulization systems. It should be noted that each double-exposure image illustrates the trajectory of the droplets during 50 μs. Fundamentally this time may be considered as a 50-μs integration time for counting the average number of droplets per unit time passing a specific point in the plasma (counts/s or frequency). The concepts and instrumentation presented are applicable to other spectrometers and nebulization systems, and may be utilized in developing a chemical analysis based on counting droplets and particles requiring no emission or mass spectrometers.

Specifically, FIG. 3 illustrates the spatial distribution characteristic for direct and indirect nebulization methods by comparing the DIHEN, operated under typical conditions, i.e. at 0.2 L/min nebulizer gas flow rate (NGFR) and 85 μL/min solution uptake rate (SUR), and the PFA nebulizer-spray chamber arrangement at a NGFR of 0.9 L/min and a SUR of 100 μL/min (natural aspiration rate). It should be noted that the outer and intermediate gases are maintained at their normal flow rates of 15 L/min and 1 L/min, respectively.

It should be noted that the exemplary implementations described below are for illustrative purposes of certain embodiments of the present invention whose capability to monitoring of the droplets inside the plasma or any other high temperature source would be readily appreciated by skilled artisans.

FIG. 3A shows that the DIHEN aerosol is scattered across the ICP torch cross-section. This effect is attributed to the large cone angle of the DIHEN aerosol and the gas dynamics inside the torch. FIG. 3B, is captured under the same operating conditions as in FIG. 3A but in the presence of the plasma, suggesting that the droplets outside of the dashed circle (5-mm i.d.) are more likely to enter the Eddy current region which is the bright area shown in FIGS. 3B and 3D, causing plasma instability and greater interferences, while the central droplets may favorably contribute to the signal. Recent studies have also revealed that the analyte ions confined to a 5-mm i.d. area at the center of the plasma contribute to the signal in ICPMS.[35,45]

In contrast to the DIHEN aerosol, the droplets emerging from the spray chamber and torch injector tube are highly confined to the center of the plasma torch, due to the small diameter of the injector tube (2 mm), and are not affected by the torch gas dynamics (FIGS. 3C and 3D). This confinement results in a more homogenous plasma, having less noise, and certainly less chemical and physical interferences. The side-on views of the torch in FIGS. 3A and 3C, respectively, clearly show the spread of droplets across the torch cross-section as compared to the narrow aerosol spatial distributions realized when the aerosol is directed to the plasma axial channel by the combination of the nebulizer-spray chamber-injector tube.

The importance of Spatial Focusing in Direct Injection will now be discussed. In order to estimate the fraction of the DIHEN aerosol entering the central channel, 100 images of the aerosol inside the torch (similar to FIG. 3A) were averaged and corrected for the background. Signal intensity was then integrated across the entire torch and inside the dashed circle. The ratio of these two quantities reveals that less than 30% of the DIHEN aerosol enters the central channel of the ICP. In interpreting the scattering images, four key points should be noted. First, Mie scattering intensity is proportional to the surface area rather than the volume of the droplets, favoring the scattering signal from smaller droplets at the center of the aerosol cone compared to that from the larger drops at the perimeters of the cone. Second, in the presence of the plasma, some droplets may move out of the integration area prior to complete evaporation occurring due to the aerosol cone divergence. Third, small droplets may not be captured with the current imaging system because of a weak scattering signal due to droplet evaporation. Fourth, the scattered light from the center of the cone is attenuated to a larger extent due to multiple scattering as it passes through denser central aerosol towards the detector. Items 1 and 2 cause a positive error in the measured fraction of the aerosol remaining in the central channel of the ICP, whereas, items 3 and 4 contribute to a negative error.

A comparison between the ICPMS sensitivities using the DIHEN and a conventional nebulizer-spray chamber setup is useful in qualitative evaluation of the error. A cross-flow nebulizer coupled to a Scott-type spray chamber is selected for this purpose because of its well-characterized transport efficiencies over a wide range of operating conditions.[46] Considering a solution uptake rate of 1 mL/min and transport efficiency of 1.7% (for a 2% nitric acid solution at 1 L/min of the nebulizer gas flow) for the conventional setup, an average 5 fold increase in sensitivities for the DIHEN (100% transport efficiency) operated at a typical solution rate of 85 µL/min is expected, if the entire aerosol is efficiently used for signal generation. However, the experimental values range from 30% to 60% of the ideal value for the same matrix (2% $HNO_3$) and nebulizer gas flow rates of 0.25-0.16 L/min.[12,47] These values are higher than the fraction of the aerosol remaining in the central channel measured by the laser scattering technique (~30%), suggesting that a negative bias is likely the dominant error in quantification of the spatial distribution. Nevertheless, confining the droplets to the central channel should increase the sensitivities with the direct injection devices, significantly reducing the noise levels and matrix effects.

Figure 4:
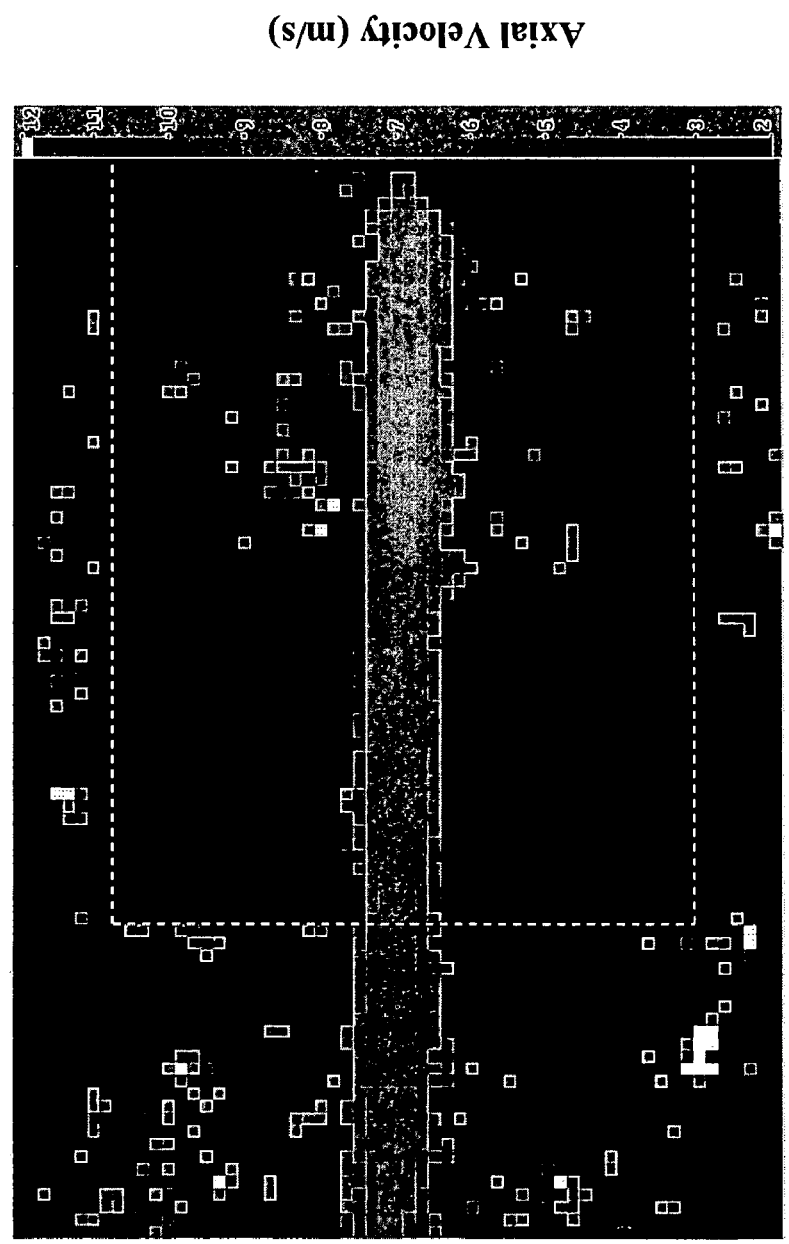
FIG. 4 is an image illustrating a velocity field of the tertiary aerosol from a PFA-spray chamber inside the ICP torch in which an outer gas flow=15 L/min, and an Intermediate gas flow 1 L/min. The dashed lines indicate the outer tube position of the torch.

Aerosol velocity will now be discussed. The velocity maps of the droplets inside the torch are obtained using PIV in the absence of the plasma. FIG. 4 illustrates the axial velocity distribution of the PFA-spray chamber aerosol inside the torch and in the presence of the intermediate and outer gas flows. FIG. 4 is similar to the velocity field previously discussed outside of the torch, further confirming that the gas dynamics at the center of the torch is mainly controlled by the injector gas flow. The same trend is observed for the DIHEN aerosol entering at the torch axial channel, however, the velocities of the droplets away from the cited axis are time-dependent. Specifically, the average velocity map does not provide a noticeable trend for the off-axis droplets.

Figure 5:
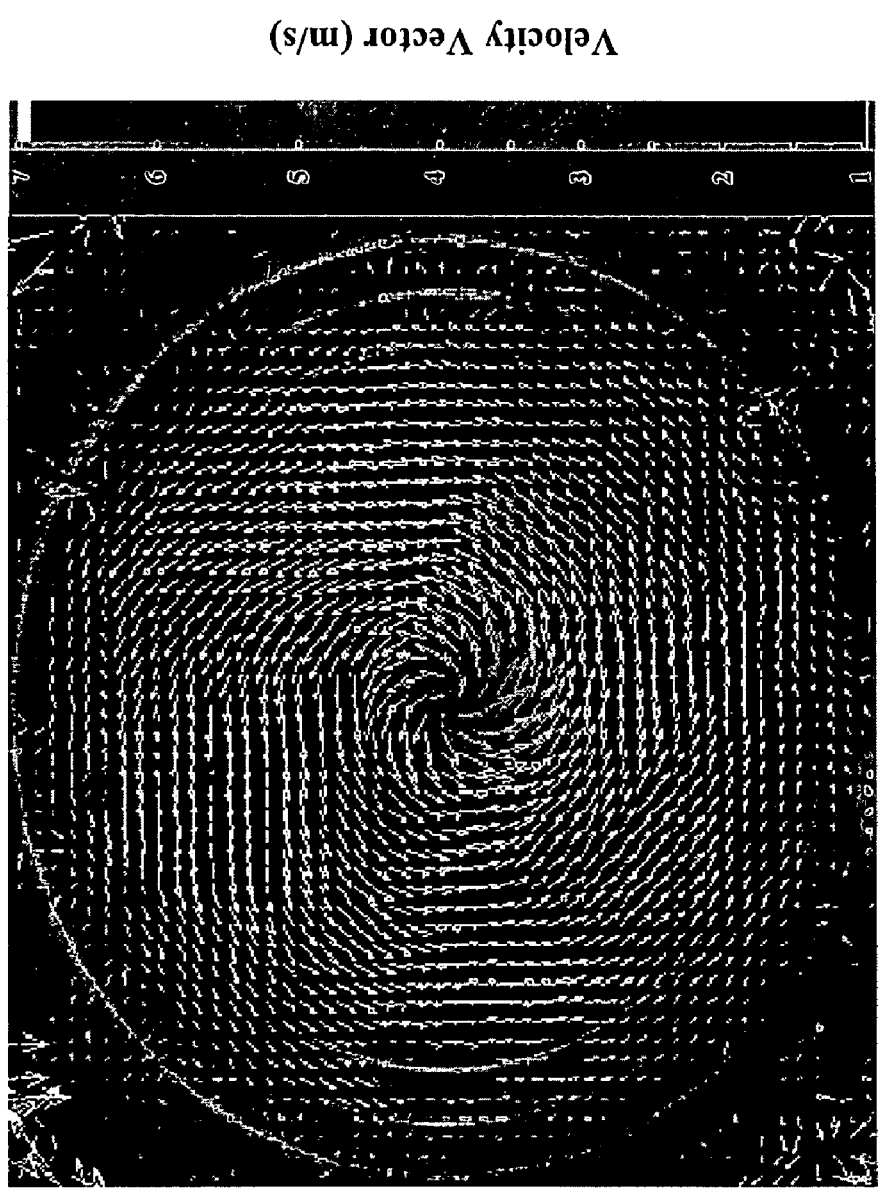
FIG. 5 is an image illustrating rotational behavior of the droplets imposed by the plasma gas at position 1 in the absence of the plasma.

Previous studies had revealed that the DIHEN aerosol rotates as it propagates from the nebulizer nozzle. The end-on PIV maps in an embodiment of the present invention show a momentary rotational behavior of the aerosol in the torch and in the absence of the outer and intermediate gases. In contrast to the previous study, however, the observed rotation is not persistent and consequently, no trend is noted in the averaged velocity maps. Note that the current results are obtained using a mathematical procedure preferably at a time resolution of 20 µs compared to visually analyzed 100-ms images in the previous study. The outer and intermediate gases, however, impose a permanent rotation on the aerosol as shown in FIG. 5. The real outcome of this rotation on droplet residence time in the plasma is uncertain at this stage, but the effect is responsible for the unusual dispersion of the droplets across the plasma tube.

Figure 6:
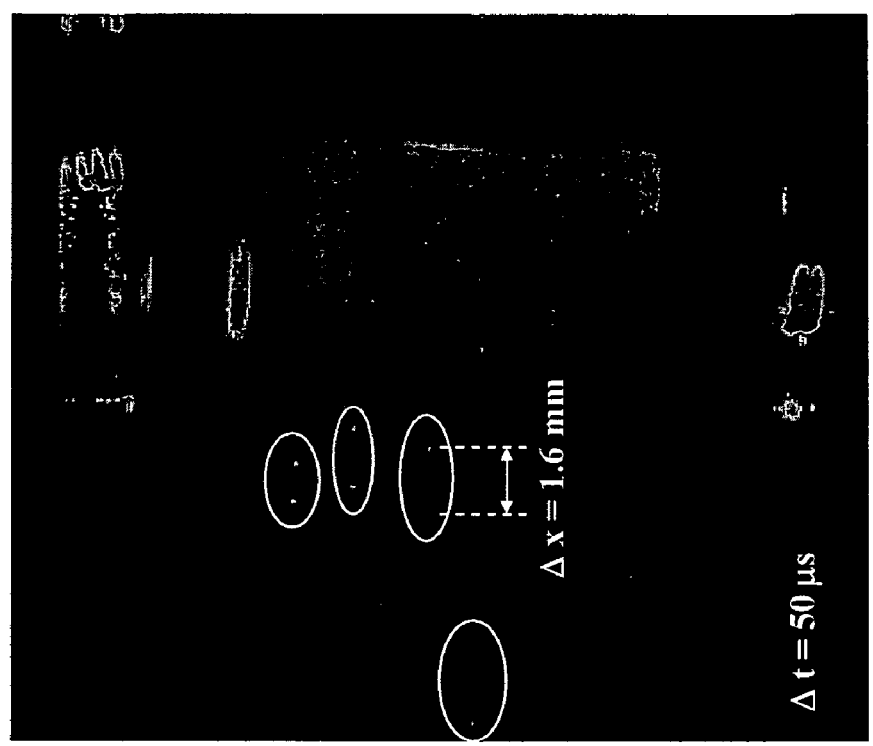
FIG. 6 is an image illustrating particle tracking velocimetry of the surviving droplets introduced by LB-DIHEN using double exposure images in an Ar ICP where the distance between the pairs indicates the displacement of the droplets during $\Delta t=50$ µs.

Surviving droplets will now be discussed. In the presence of the plasma, the droplet number density decreases dramatically, causing difficulty in PIV measurements on the remaining droplets because of the high noise in the cross-correlation plane (see FIG. 6 for the LB-DIHEN aerosol in the plasma). However, surviving droplets can be individually probed using PTV as illustrated for the LB-DIHEN in FIG. 6. Two laser shots are fired with $\Delta t=50$ µs to capture the locations of the droplets on the same image. The distance between the droplet pairs offers their displacement during the 50-µs time interval, allowing measurements of the velocity in x and y directions ($V_x$, $V_y$) from $\Delta x/\Delta t$ and $\Delta y/\Delta t$. Surviving droplets are then counted in a number of images, similar to FIG. 6, for subsequent statistical analysis. Based on theoretical calculations,[39,43] droplets smaller than 5-µm in diameter completely evaporate in a 3000-K axial channel of the argon plasma during the 50-µs probe time. Thus, it is estimated that the surviving droplets are larger than 5-µm in diameter. However, the precise measurement of the droplet diameters is not provided.

Figure 7:
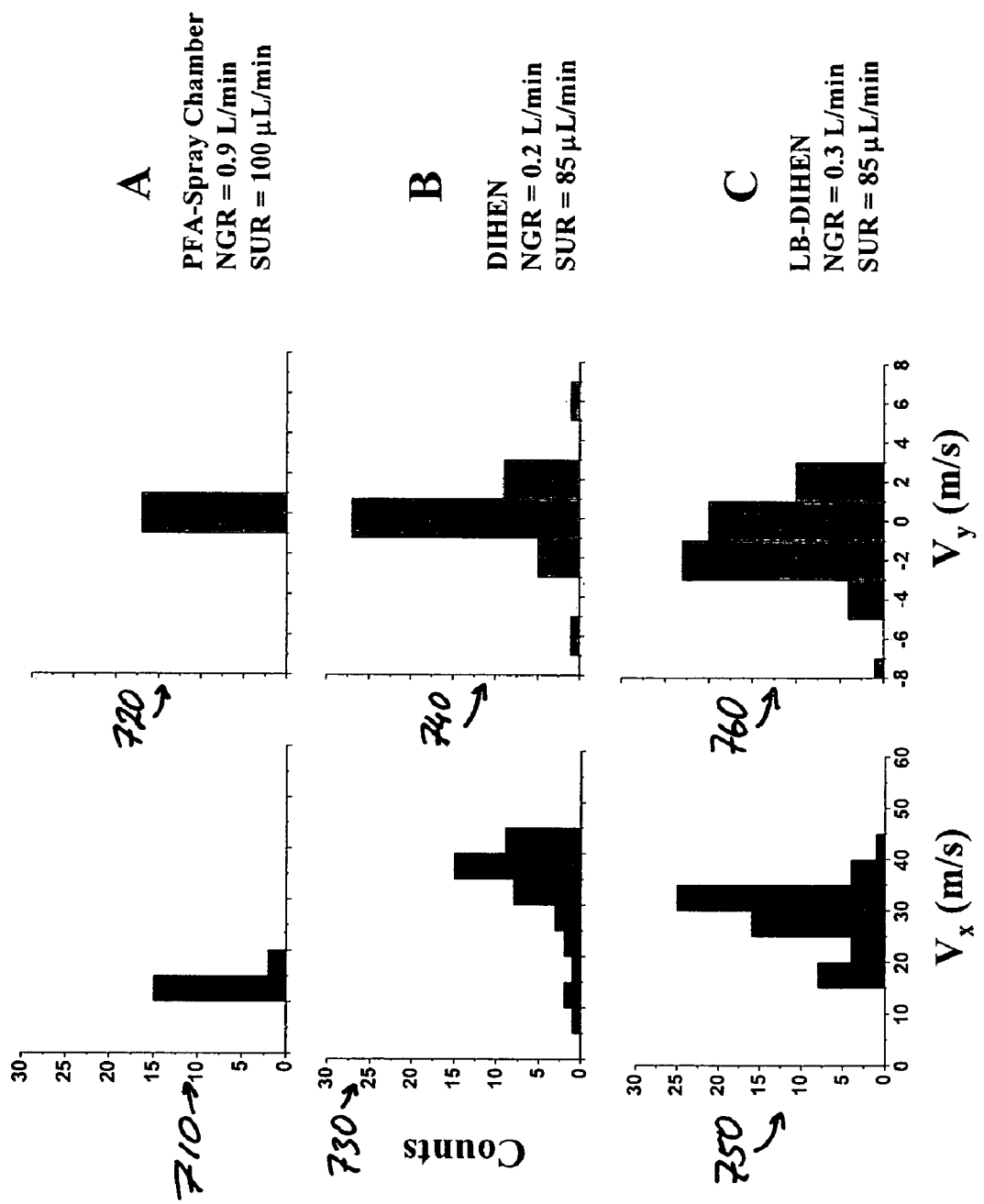
FIG. 7 is a set of bar graphs illustrating axial and radial velocity distribution of the surviving droplets in an Ar ICP introduced by: A) PFA-Spray chamber, B) DIHEN and C) LB-DIHEN.

FIG. 7 shows the histograms of surviving droplets obtained from 100 double-exposure images for the DIHEN and PFA-spray chamber arrangement and 50 images for the LB-DIHEN. It should be noted that each double-exposure image illustrates the trajectory of the droplets during 50 µs. Fundamentally this time may be considered as a 50-µs integration time for counting the average number of droplets per unit time passing a specific point in the plasma (counts/s). At this stage, the low image acquisition frequency (~4 Hz), large image file size (~1 Mbytes/image), and manual processing of the data has restricted the total number of images to 100, thus the total integration time is limited to 5 ms. For such a short integration time, a slight variation in the number of the droplets induces a very large error in the time-averaged count. Therefore, the absolute total count of the drops in FIGS. 7A-C must be considered as a qualitative estimate for each case rather than a quantitative measure. It should be noted that the presented velocity distributions are not subject to the errors arising from time averaging, thus, they are representatives of velocities of the surviving droplets. In an embodiment of the present invention, continuous-wave laser scattering form a small region in the plasma is utilized to provide a time-averaged count of the surviving droplets. In another embodiment of the present invention, pulsed laser double-exposure imaging can be used to provide important advantages over the continuous method by providing simultaneous count and velocity information throughout the entire plasma.

Droplet velocities in an indirect sample introduction will now be discussed. A very narrow radial velocity ($V_y$) distribution, with a low total count, is observed below the end of the torch tube 3 mm above the load coil for the PFA-spray chamber aerosol (FIG. 7A). This is because the PFA-spray chamber provides small tertiary droplets ($D_{3,2} \approx 4$ µm) with low axial velocity ($V_x <= 10$ m/s), strictly confined to the central channel of the ICP (see FIG. 4) due to the 2-mm diameter of the torch injector tube (Table 1). Previous studies have revealed that the typical gas velocities in the axial channel of the ICP range from 20 m/s to 25 m/s[31-35]. FIG. 7A shows a narrow axial velocity distribution (13-16 m/s) for the surviving droplets generated in this work by the PFA-spray chamber arrangement. It should be noted that these droplets travel at higher velocities compared to the values measured by PIV in the absence of the plasma (see FIG. 4), but they lag behind the axial channel gas flow in the presence of the ICP. These droplets may not be visible in the PIV images of the tertiary aerosol because of ensemble processing. To account for this effect, velocity distribution of 50,000 droplets at the center of the aerosol plum was measured by a phase Doppler particle analyzer. However, no velocities higher than 12 m/s were observed. Accordingly, it may be concluded that the tertiary droplets accelerate once they enter the axial channel of the ICP, rather they lag the gas velocity. Thus, theoretical studies that assume equal velocities in axial channel for the droplets and carrier gas may lead to improbable conclusions regarding the aerosol fate.

Droplet velocities in direct injection will now be discussed. Histograms of the DIHEN and LB-DIHEN aerosol (FIG. 7B, 7C) show, compared to the indirect sample introduction devices (FIG. 7A), a much larger number of surviving droplets and a wider radial velocity distribution. This observation is valid for the droplets from the direct injection nebulizers, which currently exhibit wider size, velocity, and spatial distributions compared to nebulization systems employing spray chambers. The larger number of the surviving droplets for the LB-DIHEN compared to the DIHEN is attributed to generally bigger droplets produced by the former.[44] The axial velocity distributions (FIG. 7B, 7C) indicate a large number of fast droplets>25 m/s for direct injection devices which survive the high temperature plasma because of their short residence time. It should be noted that these droplets travel at considerably higher velocities than the gas velocity in the ICP; therefore, this effect cannot be attributed to the acceleration of the aerosol in the plasma. In contrast to the PFA-spray chamber arrangement, the high-velocity droplets are observed in the velocity distributions produced by PDPA for both the DIHEN and LB-DIHEN in the absence of the plasma, clearly demonstrating the importance of low droplet velocity for efficient desolvation in the plasma. It should be noted, however, that the high-velocity droplets are not captured in PIV images due to ensemble averaging.

Imaging instrumentation will now be discussed. The schematic diagram of the experimental system manufactured by SprayMaster, LaVision Inc., Ypsilanti, Mich. is shown in FIG. 1. The system comprises the dual cavity frequency-doubled Nd:YAG pulsed laser 102 (120 mJ/pulse, 5 ns pulse duration, 532 nm, 15 Hz repetition rate) and a set of cylindrical lenses 104 for generating a laser sheet of about 1-mm thickness. The Mie scattering signal from the droplets is recorded by the cross-correlation charge coupled detector (CCD) 110 (1376×1040 pixels and 10 frames/sec rate) preferably accompanied by a 60-mm focal length lens manufactured by Nikon positioned at 90° angle with respect to the laser sheet. The laser and the cameras are controlled and synchronized by means of software (DaVis, LaVision Inc., Ypsilanti, Mich.) on a personal computer 106 using a programmable timing unit 108.

To reduce the background levels, a narrow band-pass notch filter 110 manufactured by 532±10 nm, Lot Oriel GmbH & Co. KG, Darmstadt, Germany is placed in the optical path to selectively transmit the laser light, blocking the intense continuum and line emission from the argon plasma. The short exposure time e.g., 1-50 μs, in conjunction with the pulsed laser 102, significantly improves the signal-to-background ratio, providing a clear snapshot of the droplets traveling in the plasma.

Particle image velocimetry (PIV) is applied to study the velocity field of the droplets inside the ICP torch in the absence of the plasma. The principles of PIV are well known to those skilled in the art and will not be discussed here.[24] Briefly, two consecutive images of moving particles are acquired using a known time lag (Δt). The images are divided into interrogation boxes and the displacement vector is calculated for each interrogation box through cross-correlation. Thus, each vector represents the momentary behavior of the ensemble of droplets in the area covered by each interrogation box. These vectors collectively represent the velocity map of the whole flow field. An average of 100 velocity fields is used to obtain the time-averaged behavior of the droplets throughout the flow field. Interrogation boxes of 32×32 pixels may be used in this study, with Δt set to 5 μs and 20 μs for side-on and end-on views, respectively.

In the presence of the plasma, most of the droplets evaporate, resulting in a significant reduction in the droplet number density from the injection nozzle towards the analytical zone. In order to examine the velocity of the individual surviving droplets, the exposure time is adjusted to capture the scattering of two laser pulses, fired using a known time lag (Δt), on the same image. The resulting double exposure image includes pairs of droplets separated by a distance corresponding to the displacement of individual drops during Δt. It should be noted that the camera must be pre-calibrated against a target in order to calculate the displacement and velocity vectors. An exemplary target used is a 5 cm×5 cm square filled with equally spaced 2-mm apart dots.

ICP instrumentation and operating conditions will now be discussed. The instrumentation and operating conditions for the ICP and sample introduction systems are shown in Table 1. A radio frequency (RF) power of 1300 W, which is typical for indirect sample introduction is maintained to compare the direct and indirect sample introduction methods, although the optimum RF power for direct injection nebulizers is 1500 W or higher. The sample introduction systems explored included: 1) the DIHEN, 2) the LB-DIHEN, and 3) PFA100-spray chamber. Distilled-deionized water (18.3 MΩcm resistivity) is used to produce the aerosol.

TABLE 1

Operating conditions for ICP Instrument and sample introduction systems.

| ICP system | |
|---|---|
| RF Generator | PE-Sciex Elan 5000 (Perkin-Elmer Corporation, Norwalk, CT) |
| RF power, W | 1300 |
| Nominal frequency, MHz | 32 |
| RF generator type | Free-running |
| Induction coil circuitry | 3-turn coil, Electronically balanced, PlasmaLok ® |
| Torch dimensions, mm | Outer tube o.d. = 20; Outer tube i.d. = 18 Intermediate tube o.d. = 16; Intermediate tube i.d. = 14 Injector tube i.d. = 2 (for indirect sample introduction) |
| Nebulizer/injector tip position Outer gas flow rate, L/min | 2 mm below the intermediate tube 15, controlled by a Matheson gas flow meter (Model MFMR-0800-AA; 605, Matheson Gas Products, East Rutherford, NJ) |
| Intermediate gas flow rate, L/min | 1, controlled by a Matheson gas flow meter (Model MFMR-0800-AA; 603, Matheson Gas Products) |
| Sample introduction systems | |
| Nebulizers | 1) DIHEN (Model DIHEN-170-AA, Meinhard Glass Products, Analytical Reference Materials International Corp., Golden, Co) 2) Large Bore-DIHEN (Model LB-DIHEN-30-AA, Meinhard Glass Products, Analytical Reference Materials International Corp.) |

TABLE 1-continued

Operating conditions for ICP Instrument and sample sample introduction systems.

| | |
|---|---|
| | 3) PFA-100 fixed-capillary microflow nebulizer with a PFA PureChamber spray chamber (137-mL internal volume, Elemental Scientific, Inc., Omaha, NE) |
| Nebulizer gas flow rate, L/min | 1) 0.2 for the DIHEN<br>2) 0.3 for the LB-DIHEN<br>3) 0.9 for the PFA controlled by a mass flow meter (Model 8200, Matheson Gas Products) |
| Solution uptake rate, μL/min | 1) 85 (for the DIHEN and LB-DIHEN), controlled by a syringe pump (Model KDS100, KD Scientific, New Hope, PA) and PEEK pump tubing (0.010-in. i.d.; Upchurch Scientific, Oak Harbor, WA)<br>2) 100 (for the PFA with natural aspiration) |

Thus, the foregoing description of exemplary embodiments of the present invention is intended to be illustrative, and not to limit the scope of the invention which is defined by the claims and their equivalents. Many alternatives, modifications and variations will be apparent to those skilled in the art. In this regard, the concepts and instrumentation described herein may be applicable to various spectrometers and droplet sources, and may be utilized in developing chemical analysis based on counting droplets and particles requiring no emissions or mass spectrometers. For example, the concepts described herein may be implemented in automobile industry and/or aerospace industry for designing engines with optimum fuel consumption efficiency.

REFERENCES

[1] A. Montaser, Ed. Inductively Coupled Plasma Mass Spectrometry; VCH-Wiley: New York, (1998).

[2] A. Montaser, and D. W. Golightly, Eds. Inductively Coupled Plasmas in Analytical Atomic Spectrometry, 2nd ed.; Wiley-VCH: New York, (1992).

[3] A. Montaser, J. A. McLean, H. Liu, and J.-M. Mermet, "An introduction to ICP spectrometries for elemental analysis", in Inductively Coupled Plasma Mass Spectrometry, ed. A. Montaser, Wiley-VCH, New York, USA, pages 1-31 (1998).

[4] A. Montaser, M. G. Minnich, J. A. McLean, H. Liu, J. A. Caruso, and C. W. McLeod, "Sample introduction in ICPMS", in Inductively Coupled Plasma Mass Spectrometry, ed. A. Montaser, Wiley-VCH, New York, USA, pages 83-264 (1998).

[5] A. Montaser, M. G. Minnich, H. Liu, A. G. T. Gustavson, and R. F. Browner, "Fundamental aspects of sample introduction in ICP spectrometry", in Inductively Coupled Plasma Mass Spectrometry, ed. A. Montaser, Wiley-VCH, New York, USA, pages 335-420 (1998).

[6] J. A. McLean, M. G. Minnich, L. A. Iacone, H. Liu, and A. Montaser, Nebulizer diagnostics: fundamental parameters, challenges, and techniques on horizon, J. Anal. Atom. Spectrom. 13, 829-842 (1998).

[7] A. G. T. Gustavson, "Liquid sample introduction into plasmas" in Inductively Coupled Plasma in Analytical Atomic Spectrometry, $2^{nd}$ edn., Ed. A. Montaser, and D. W. Golightly, Wiley-VCH, New York, USA, pages 690-720 (1992).

[8] R. F. Browner, "Fundamental aspects of aerosol generation and transport, in Inductively Coupled Plasma Emission Spectroscopy, Ed. P. W. J. M. Boumans, Wiley-VCH, New York, USA, part II, pages 244-288 (1987).

[9] J.-L. Todoli, and J.-M. Mermet, Acid interferences in atomic spectrometry: analyte signal effects and subsequent reduction, Spectrochim. Acta 54B, 895-929 (1999).

[10] E. Bjorn, and W. Frech, Non-spectral interference effects in inductively coupled plasma mass spectrometry using direct injection high efficiency and microconcentric nebulization, J. Anal. Atom. Spectrom. 16, 4-11 (2001). 12

[11] K. E. Lawrence, G. W. Rice, and V. Fassel, Direct injection sample introduction for flow injection analysis and liquid chromatography with inductively coupled argon plasma spectrometric detection, Anal. Chem. 56, 289-292 (1984).

[12] J. A. McLean, H. Zhang, and A. Montaser, A direct injection high-efficiency nebulizer for inductively coupled plasma mass spectrometry, Anal. Chem. 70, 1012-1020 (1998).

[13] V. Majidi, J. Quarnstrom, Q. Tu, W. Frech, and Y. Thomassen, Improving sensitivity for CE-ICP-MS using multicapillary parallel separation, J. Anal. Atom. Spectrom. 14, 1933-1935 (1999).

[14] B. W Acon, J. A. McLean, and A. Montaser, A direct injection high efficiency nebulizer for micro-bore high performance liquid chromatography-inductively coupled plasma mass spectrometry, J. Anal. Atom. Spectrom. 16, 852-857 (2001).

[15] M. Wind, A. Eisenmenger, and W. D. Lehmann, Modified direct injection high efficiency nebulizer with minimized dead volume for the analysis of biological samples by micro- and nano-LC-ICP-MS, J. Anal. Atom. Spectrom. 17, 21-26 (2002).

[16] J.-L. Todoli, and J.-M. Mermet, Evaluation of a direct injection high-efficiency nebulizer (DIHEN) by comparison with a high-efficiency nebulizer (HEN) coupled to a cyclonic spray chamber as a liquid sample introduction system for ICP-AES, J. Anal. At. Spectrom. 16, 514-520 (2001).

[17] R. H. Clifford, I Ishii, A. Montaser, and G. A. Meyer, Dual-beam, light-scattering interferometry for simultaneous measurements of droplet-size and velocity distributions of aerosols from commonly used nebulizers, Anal. Chem. 62, 390-394 (1990).

[18] S. C. K. Shum, S. K. Johnson, H.-M. Pang, and R. S. Houk, Spatially resolved measurements of size and velocity distributions of aerosol droplets from a direct injection nebulizer, Appl. Spectrosc. 47, 575-583 (1993).

[19] A. Montaser, and H. Liu, Phase-Doppler diagnostic studies of primary and tertiary aerosols produced by a high-efficiency nebulizer, Anal. Chem. 66, 3233-3242 (1994).

[20] J. W. Olesik, J. A. Kinzer, and G. J. McGowan, Observation of atom and ion clouds produced from single droplets of sample in inductively coupled plasmas by optical emission and laser-induced fluorescence imaging, Appl. Spectrosc. 51, 607-616 (1997).

[21] J. A. McLean, R. A. Huff, and A. Montaser, Fundamental properties of aerosol produced in helium by a direct injection nebulizer, Appl. Spectrosc. 53, 1331-1339 (1999).

[22] J. A. McLean, M. G. Minnich, A. Montaser, J. Su, and W. Lai, Optical patternation: a technique for three-dimensional aerosol diagnostics, Anal. Chem. 72, 4796-4804 (2000).

[23] M. G. Minnich, J. A. McLean, and A. Montaser, Spatial aerosol characteristics of a direct injection high efficiency nebulizer via optical patternation, Spectrochim. Acta 56B, 1113-1126 (2001).

24. K. Kahen, K. Jorabchi, C. Gray, and A. Montaser, Spatial mapping of droplet velocity and size in direct and indirect nebulization, Anal. Chem. 76, 7194-7201 (2004).
25. J. W. Olesik, Investigation of the fate of individual sample drops in inductively coupled plasmas, Appl. Spectrosc. 51, 158A-175A (1997).
26. J. W. Olesik, and J. C. Fister III, Incompletely desolvated droplets in argon inductively coupled plasmas: their number, original size and effect on emission intensities, Spectrochim. Acta46B, 851-868 (1991).
27. S. E. Hobbs, and J. W. Olesik, Inductively coupled plasma mass spectrometry signal fluctuations due to individual aerosol droplets and vaporizing particles, Anal. Chem. 64, 274-83 (1992).
28. S. E. Hobbs, and J. W. Olesik, The effect of desolvating aerosol and vaporizing particles on ionization and excitation in Ar inductively coupled plasma, Spectrochim. Acta 48 B, 817-833 (1993).
29. S. E. Hobbs, and J. W. Olesik, The influence of incompletely desolvated droplets and vaporizing particles on chemical matrix effects in inductively coupled plasma spectrometry: time-gated optical emission and laser-induced fluorescence measurements, Spectrochim. Acta 52B, 353-367 (1997).
30. A. Lazar, and P. B. Farnsworth, Matrix effect studies in inductively coupled plasmas with monodisperse droplets. Part I: the influence of matrix on the vertical analyte emission profile, Appl. Spectrosc. 53, 457-464 (1999).
31. R. S. Houk, R. K. Winge, and X. Chen, High speed photographic study of wet droplets and solid particles in the inductively coupled plasma, J. Anal. Atom. Spectrom. 12, 1139-1148 (1997).
32. D. B. Aeschliman, S. J. Bajic, D. P. Baldwin, and R. S. Houk, High-speed digital photographic study of an inductively coupled plasma during laser ablation: comparison of dried solution aerosols from a microconcentric nebulizer and solid particles from laser ablation, J. Anal. Atom. Spectrom. 18, 1008-1014 (2003).
33. M. T. Cicerone, and P. B. Farnsworth, A simple non-invasive method for the measurement of gas velocities in an inductively coupled plasma, Spectrochim. Acta 44B, 897-907 (1989).
34. M. P. Dziewatkoski, L. B. Daniels, and J. W. Olesik, Time-resolved inductively coupled plasma mass spectrometry measurements with individual, monodisperse drop sample introduction, Anal. Chem. 68, 1101-1109 (1996).
35. I. I. Stewart, C. E. Hensman, and J. W. Olesik, Influence of gas sampling on analyte transport within the ICP and ion sampling for ICPMS studied using individual, isolated sample droplets, Appl. Spectrosc. 54, 164-174 (2000).
36. E. Thomas Jr., Direct measurement of two-dimensional velocity profiles in direct current glow discharge dusty plasmas, Phys. Plasmas 6, 2672-2675 (1999).
37. L. Zimmer, and Y. Ikeda, Planar droplet sizing for the characterization of droplet clusters in an industrial gun-type burner, Part. Part. Syst. Charact. 20 199-208 (2003).
38. J C. Cabalo, J. Scmidt, J. O. L. Wendt, and A. Scheeline, Spectrometric method for characterizing drop and powder trajectories and chemistry in reactive flows, Appl. Spectrosc. 56, 1346-1353 (2002).
39. C. M. Benson, S. F. Gimelshein, D. A. Levin, and A. Montaser, Simulation of droplet heating and desolvation in an inductively coupled plasma—Part I, Spectrochimica Acta 56B, 1097-1112 (2001).
40. J. A. Horner, S. A. Lehn, and G. M. Hieftje, Computerized simulation of aerosol-droplet desolvation in an inductively coupled plasma, Spectrochim. Acta 57B, 1025-1042 (2002).
41. C. M. Benson, J. Zhong, S. F. Gimelshein, D. A. Levin, and A. Montaser, Simulation of droplet heating and desolvation in an inductively coupled plasma—Part II: coalescence in the plasma, Spectrochimica Acta 58B, 1453-1471 (2003).
42. Y. Shan, and J. Mostaghimi, Numerical simulation of aerosol droplets desolvation in a radio frequency inductively coupled plasma, Spectrochim. Acta 58B, 1959-1977 (2003).
43. C. M. Benson, D. A. Levine, J. Zhong, S. F. Gimelshein, and A. Montaser, Kinetic model for aerosol droplets in high-temperature environments, J. Thermophys. Heat Transfer 18, 122-134 (2004).
44. B. W. Acon, J. A. McLean, and A. Montaser, A large bore-direct injection high efficiency nebulizer for inductively coupled plasma spectrometry, Anal. Chem. 72, 1885-1893 (2000).
45. J. H. Macedone, A. A. Mills, and P. B. Farnsworth, Optical measurement of ion trajectories through the vacuum interface of inductively coupled plasma mass spectrometry, Appl. Spectrosc. 58, 463-467 (2004).
46. I. I. Stewart, and J. W. Olesik, The effect of nitric acid concentration and nebulizer gas flow on aerosol properties and transport rates in inductively coupled plasma sample introduction, J. Anal. Atom. Spectrom. 13, 1249-1256 (1998).
47. C. S. Westphal, K. Kahen, W. F. Rutkowski, B. W. Acon, and A. Montaser, Demountable direct injection high efficiency nebulizer for inductively coupled plasma mass spectrometry, Spectrochim. Acta 59B, 353-368 (2004).

We claim:

1. A self-tuning spectrometer comprising a system for in-situ droplet monitoring, the system comprising:
    a laser light delivery system for delivering at least two laser pulses to at least one of droplets, particles and aerosol;
    a detector for capturing a scattering of the laser pulses from the at least one of droplets, particles and aerosol;
    an image acquisition unit for receiving and processing data from the detector; and
    a system controller for synchronizing the laser delivery system and the detector, whereby the scattering of the laser pulses from the at least one of droplets, particles and aerosol is processed to monitor properties of the at least one of droplets, particles and aerosol;
    wherein operating parameters of at least one of (1) the self-tuning spectrometer, (2) a source of the at least one of droplets, particles and aerosol and (3) a plasma source or a high temperature source are optimized based on the monitored properties of the at least one of droplets, particles and aerosol.

2. The system as claimed in claim 1, wherein the properties comprise at least one of velocity, size and number density.

3. The system as claimed in claim 1, wherein the laser light delivery system comprises:
    a dual cavity frequency-doubled Nd: YAG pulsed laser;
    a mirror; and
    a cylindrical lens;
    wherein the dual cavity frequency-doubled Nd: YAG pulsed laser, the mirror and the cylindrical lens are configure to generate a laser sheet.

4. The system as claimed in claim 1, wherein the delivering of the at least two laser pulses comprises delivering a laser sheet.

5. The system as claimed in claim 1, wherein the detector comprises a charged coupled detector (CCD).

6. The system as claimed in claim 5, further comprising a notch filter configured in an optical path between the CCD and the at least one of droplets, particles and aerosol.

7. The system as claimed in claim 6, wherein the notch filer is a narrow band-pass notch filter.

8. The system as claimed in claim 1, wherein the laser light delivery system delivers the at least two pulses at a time lag of about 50 microseconds.

9. The system as claimed in claim 1, wherein the system controller comprises a microcomputer.

10. The system as claimed in claim 1, further comprising a programmable timing unit connected to the laser light delivery system and the detector, the programmable timing unit being controllable by the system controller to facilitate the synchronizing of the laser delivery system and the detector.

11. A system for in-situ droplet monitoring, the system comprising:
a laser light delivery system for delivering at least two laser pulses to at least one of droplets, particles and aerosol;
a detector for capturing a scattering of the laser pulses from the at least one of droplets, particles and aerosol;
an image acquisition unit for receiving and processing data from the detector; and
a system controller for synchronizing the laser delivery system and the detector, whereby the scattering of the laser pulses from the at least one of droplets, particles and aerosol is processed to monitor properties of the at least one of droplets, particles and aerosol;
wherein:
the detector comprises a charged coupled detector (CCD); and
the CCD comprises a cross-correlation CCD and a 60-millimeter focal lens positioned at about a 90-degree angle with respect to the laser.

12. The system as claimed in claim 1, wherein the droplets are produced by at least one of direct and indirect nebulization, and are output from a nebulizer.

13. The system as claimed in claim 1, wherein the at least one of droplets, particles and aerosol are produced and output by a first source of the at least one of droplets, particles and aerosol.

14. The system as claimed in claim 13, wherein the at least one of droplets, particles and aerosol interact with at least one of a plasma source and a heat source.

15. The system as claimed in claim 14 further comprising:
a feedback line coupled to at least one of the first source, the plasma source and the heat source;
a controller coupled to the feedback line; and
a control line coupled to the system controller;
wherein a feedback from the at least one of the first source, the plasma source and the heat source via the feedback line, the controller and the control line facilitate control of operating parameters of the at least one of (1) the first source, and (2) the plasma source or the heat source based on the monitored properties of the at least one of droplets, particles and aerosol.

16. The system as claimed in claim 15, wherein the operating parameters comprise at least one of a flow rate of the at least one of droplets, particles and aerosol, and a physical configuration of the at least one of the first source, the plasma source and the heat source.

17. A method for in-situ monitoring of droplets in a plasma, comprising:
delivering at least two laser pulses to at least one of droplets, particles and aerosol;
capturing a scattering of the laser pulses from the at least one of droplets, particles and aerosol; and
processing the scattering of the laser pulses from the at least one of droplets, particles and aerosol to monitor properties of the at least one of droplets, particles and aerosol,
wherein the scattering comprises continuous-wave laser scattering from a small region in the plasma, and the processing comprises providing a time-averaged count of the at least one of droplets, particles and aerosol.

18. The method as claimed in claim 17, wherein the delivering of the at least two laser pulses comprises generating a laser sheet.

19. The method as claimed in claim 18, wherein the laser sheet comprises a thickness of about 1 millimeter.

20. The method as claimed in claim 17, wherein the capturing of the scattering of the laser pulses comprising arranging a charged coupled detector (CCD) in an optical path of the laser pulses scattered from the at least one of droplets, particles and aerosol.

21. The method as claimed in claim 20, wherein the capturing of the scattering of the laser pulses further comprises configuring a notch filter in the optical path between the CCD and the droplet.

22. The method as claimed in claim 21, wherein the notch filer is a narrow band-pass notch filter.

23. The method as claimed in claim 22, wherein the delivering of the at least two laser pulses comprises delivering the at least two pulses at a time lag of about 50 microseconds.

24. The method as claimed in claim 17, further comprising synchronizing the delivering of the at least two laser pulses and the capturing of the scattering of the laser pulses.

25. A method for in-situ droplet monitoring, comprising:
delivering at least two laser pulses to at least one of droplets, particles and aerosol;
capturing a scattering of the laser pulses from the at least one of droplets, particles and aerosol; and
processing the scattering of the laser pulses from the at least one of droplets, particles and aerosol to monitor properties of the at least one of droplets, particles and aerosol;
wherein the capturing of the scattering of the laser pulses comprises arranging a cross-correlation charged coupled detector (CCD) in an optical path of the laser pulses scattered from the at least one of droplets, particles and aerosol, the method further comprising positioning a 60-millimeter focal lens at about a 90-degree angle with respect to the laser.

26. The method as claimed in claim 17, wherein the droplets are produced by at least one of direct and indirect nebulization, and are output from a nebulizer.

27. The method as claimed in claim 17, wherein the at least one of droplets, particles and aerosol are produced by a first source, and output from a second source.

28. The method as claimed in claim 27, wherein the at least one of droplets, particles and aerosol interact with at least one of a plasma source and a heat source.

29. The method as claimed in claim 28 further comprising:
receiving feedback from at least one of the first source, the second source, the plasma source and the heat source indicative of the operating properties of the at least one of the first source, the second source, the plasma source and the heat source; and
controlling the operating parameters of the at least one of the (1) the source of the at least one of droplets, particles and aerosol, and (2) the plasma source or the heat source based on the monitored properties of the at least one of droplets, particles and aerosol.

30. A method for in-situ droplet monitoring, comprising:
delivering at least two laser pulses to at least one of droplets, particles and aerosol;
capturing a scattering of the laser pulses from the at least one of droplets, particles and aerosol; and
processing the scattering of the laser pulses from the at least one of droplets, particles and aerosol to monitor properties of the at least one of droplets, particles and aerosol;
wherein:
the at least one of droplets, particles and aerosol are produced by a first source, and output from a second source; and
the at least one of droplets, particles and aerosol interact with at least one of a plasma source and a heat source;
the method further comprising:
receiving feedback from at least one of the first source, the second source, the plasma source and the heat source indicative of the operating properties of the at least one of the first source, the second source, the plasma source and the heat source; and
controlling the operating parameters of the at least one of the (1) the source of the at least one of droplets, particles and aerosol, and (2) the plasma source or the heat source based on the monitored properties of the at least one of droplets, particles and aerosol;
wherein the operating parameters comprise at least one of a flow rate of the at least one of droplets, particles and aerosol, and a physical configuration of the at least one of (1) the source of the at least one of droplets, particles and aerosol, and (2) the plasma source or the heat source.

31. A method for in-situ droplet monitoring, comprising:
delivering at least two laser pulses to at least one of droplets, particles and aerosol;
capturing a scattering of the laser pulses from the at least one of droplets, particles and aerosol; and
processing the scattering of the laser pulses from the at least one of droplets, particles and aerosol to monitor properties of the at least one of droplets, particles and aerosol
wherein:
the droplets are produced by at least one of direct and indirect nebulization, and are output from a nebulizer; and
the droplet interact with a plasma from an inductively coupled plasma (ICP) torch.

32. The method as claimed in claim 31, wherein the delivering of the at least two laser pulses comprises at least one of:
generating and delivering a laser sheet 1 millimeter downstream of an intermediate tube where the droplets enter into the plasma to study an in-situ behavior of the droplets in the presence and absence of the plasma;
generating and delivering a laser sheet at a top turn of a load coil to study a contribution to at least one of noise levels, loss of signal, physical and chemical interferences, and matrix effects; and
generating and delivering a laser sheet 10 millimeters above the load coil in ICP mass spectrometry (ICPMS), wherein ions are extracted into a vacuum interface.

33. The method as claimed in claim 25, wherein the capturing of the scattering of the laser pulses from the at least one of droplets, particles and aerosol comprises using an exposure time of about 50 microsecond.

34. The method as claimed in claim 17, wherein the processing comprises counting an average number of the at least one of droplets, particles and aerosol per unit time passing a specific point.

35. The method as claimed in claim 31, wherein the processing comprises obtaining velocity maps of the droplets inside the torch using particle image velocimetry (PIV) in the absence of the plasma.

36. The method as claimed in claim 34, wherein the processing further comprises using a mathematical procedure at a time resolution of 20 microseconds.

37. The method as claimed in claim 17, wherein:
the delivering of the at lest two laser pulses comprises generating two laser pulse with a time interval of 50 microseconds therebetween; and
the capturing of the scattering of the laser pulses comprises capturing locations of the at least one of droplets, particles and aerosol on the same image, wherein a distance between at least one pair of the at least one of droplets, particles and aerosol during the time interval of 50 microseconds is measured; and
the processing comprises obtaining measurements of a velocity in x and y directions.

38. The method as claimed in claim 17, wherein the processing further comprises estimating a diameter of the at least one of droplets, particles and aerosol.

39. The method as claimed in claim 17, wherein the capturing comprises pulsed laser double-exposure imaging, and the processing comprises providing simultaneous count and velocity information.

40. The system as claimed in claim 1, wherein the at least one of droplets, particles and aerosol are produces by at least one of a nebulizer, a fuel injector and an inhaler.

41. The method as claimed in claim 17, wherein the at least one of droplets, particles and aerosol are produces by at least one of a nebulizer, a fuel injector and an inhaler.

42. A method for tuning a spectrometer while performing in-situ droplet monitoring, the method comprising:
delivering at least two laser pulses to at least one of droplets, particles and aerosol;
capturing a scattering of the laser pulses from the at least one of droplets, particles and aerosol;
processing the scattering of the laser pulses from the at least one of droplets, particles and aerosol to monitor properties of the at least one of droplets, particles and aerosol; and
utilizing the monitored properties of the at least one of droplets, particles and aerosol to optimize operating parameters of at least one of (1) the spectrometer, (2) a source of the at least one of droplets, particles and aerosol and (3) a plasma source or a high temperature source.

43. The system as claimed in claim 4, wherein the laser sheet comprises a thickness of about 1 millimeter.

* * * * *

UNITED STATES PATENT AND TRADEMARK OFFICE
CERTIFICATE OF CORRECTION

PATENT NO. : 7,804,064 B2  
APPLICATION NO. : 11/240642  
DATED : September 28, 2010  
INVENTOR(S) : Montaser et al.

Page 1 of 1

It is certified that error appears in the above-identified patent and that said Letters Patent is hereby corrected as shown below:

On the Title page of the patent, item (60), "60/615,542" should be changed to "60/614,542".

In Column 1, line 12 of the patent, "60/615,542" should be changed to "60/614,542".

Signed and Sealed this  
Eleventh Day of October, 2011

David J. Kappos  
*Director of the United States Patent and Trademark Office*